United States Patent [19]
Barlow

[11] 3,950,377
[45] Apr. 13, 1976

[54] DIPHENYLAMINE DERIVATIVES
[75] Inventor: Charles Brian Barlow, Camberley, England
[73] Assignee: Imperial Chemical Industries Limited, London, England
[22] Filed: Apr. 15, 1974
[21] Appl. No.: 461,219

Related U.S. Application Data
[63] Continuation-in-part of Ser. No. 425,279, Dec. 17, 1973, abandoned.

[30] Foreign Application Priority Data

| Dec. 20, 1972 | United Kingdom | 58692/72 |
| Feb. 9, 1973 | United Kingdom | 6393/73 |
| Feb. 9, 1973 | United Kingdom | 6394/73 |
| Feb. 9, 1973 | United Kingdom | 6395/73 |
| May 15, 1973 | United Kingdom | 23046/73 |
| May 15, 1973 | United Kingdom | 23047/73 |
| Feb. 9, 1973 | United Kingdom | 6392/73 |

[52] U.S. Cl. ............. 260/465 E; 260/576; 424/304; 424/330
[51] Int. Cl.² ............. C07C 121/78; C07C 87/50
[58] Field of Search ............. 260/465 E, 576

[56] References Cited
UNITED STATES PATENTS

| 3,637,796 | 1/1972 | Battershell | 260/465 E |
| 3,681,425 | 8/1972 | Kiehs et al. | 260/465 E |
| 3,764,624 | 10/1973 | Strong et al. | 260/576 X |

Primary Examiner—Joseph Paul Brust
Assistant Examiner—Dolph H. Torrence
Attorney, Agent, or Firm—Cushman, Darby & Cushman

[57] ABSTRACT
A group of 4-cyano-or 4-trifluoromethyl-2,6 dinitrodiphenylamine derivatives are very toxic to a wide variety of insect and other invertebrate pests.

5 Claims, No Drawings

DIPHENYLAMINE DERIVATIVES

This is a continuation-in-part of application Ser. No. 425,279, filed Dec. 17, 1973, now abandoned.

This invention relates to novel diphenylamine derivatives, and more particularly it relates to novel diphenylamine derivatives having use as pesticidal agents.

Accordingly the present invention provides diphenylamine derivatives of formula:

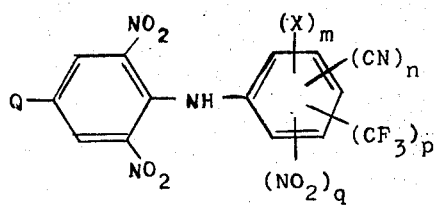

wherein either (a) Q represents a cyano or trifluoromethyl group, and X represents a halogen atom, $m$ is an integer from zero to three, $n$ is zero or one, $p$ is an integer from zero to two, and $q$ is an integer from zero to three, the sum of $m$, $n$, $p$ and $q$ being an integer from two to five; or (b) Q represents a nitro group and X represents a halogen atom, $m$ is an integer from zero to three, $n$ is zero or one, $p$ is an integer from zero to two, $q$ is an integer from zero to three, the sum of $n$ and $p$ being an integer from one to three and the sum of $m$, $n$, $p$ and $q$ being an integer from two to five.

A preferred group of diphenylamine derivatives, according to the present invention are those of formula:

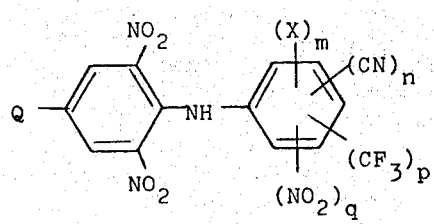

wherein Q represents a cyano or trifluoromethyl group, and X represents a halogen atom, $m$ is an integer from zero to three, $n$ is zero or one, $p$ is an integer from zero to two, and $q$ is an integer from zero to three, the sum of $m$, $n$, $p$ and $q$ being an integer from two to five.

Compounds according to the invention include those set out in table I below, where the values for Q, $R^1$, $R^2$, $R^3$, $R^4$ and $R^5$ are given. The compounds conform to the formula:

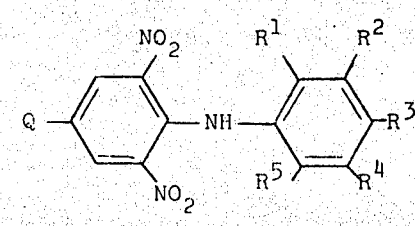

TABLE I

| Compound No | Q | $R^1$ | $R^2$ | $R^3$ | $R^4$ | $R^5$ |
|---|---|---|---|---|---|---|
| 1 | CF₃ | Cl | H | NO₂ | H | Cl |
| 2 | CN | Cl | H | NO₂ | H | Cl |
| 3 | CF₃ | NO₂ | H | NO₂ | H | H |
| 4 | CF₃ | CF₃ | H | NO₂ | H | H |
| 5 | CF₃ | Cl | H | Cl | H | Cl |
| 6 | CN | CF₃ | H | NO₂ | H | H |
| 7 | NO₂ | CF₃ | H | NO₂ | H | H |
| 8 | CF₃ | NO₂ | H | CF₃ | H | H |
| 9 | CF₃ | Cl | H | Cl | H | H |
| 10 | CF₃ | Cl | H | H | H | Cl |
| 11 | CF₃ | Cl | H | NO₂ | H | NO₂ |
| 12 | CF₃ | Cl | H | NO₂ | H | H |
| 13 | CF₃ | NO₂ | H | CF₃ | H | NO₂ |
| 14 | NO₂ | Cl | H | CF₃ | H | H |
| 15 | CF₃ | NO₂ | H | CN | H | NO₂ |
| 16 | CF₃ | Cl | H | NO₂ | Cl | H |
| 17 | CN | Br | H | CF₃ | H | Br |
| 18 | CF₃ | Cl | H | NO₂ | H | Br |
| 19 | CN | CF₃ | H | NO₂ | H | Br |
| 20 | CF₃ | NO₂ | H | NO₂ | H | NO₂ |
| 21 | CN | CF₃ | H | NO₂ | H | NO₂ |
| 22 | CF₃ | H | CF₃ | H | CF₃ | H |
| 23 | CF₃ | Br | H | CN | H | Br |
| 24 | CF₃ | CF₃ | H | NO₂ | H | NO₂ |
| 25 | CF₃ | Br | H | NO₂ | H | Br |
| 26 | CF₃ | CF₃ | H | NO₂ | H | Br |
| 27 | CF₃ | NO₂ | CF₃ | H or NO₂ | CF₃ | NO₂ or H |
| 28 | CF₃ | Br | Cl | NO₂ | H | Cl |
| 29 | CF₃ | Cl | Cl | NO₂ | H | Cl |
| 30 | CF₃ | NO₂ | H | NO₂ | H | Br |
| 31 | CF₃ | NO₂ | H | Br | H | Br |
| 32 | NO₂ | H | CF₃ | H | CF₃ | H |
| 33 | CF₃ | Cl | Cl | H | H | H |
| 34 | CF₃ | Cl | H | Cl | NO₂ | NO₂ |
| 35 | CF₃ | CF₃ | H | NO₂ | H | Cl |
| 36 | NO₂ | Cl | CF₃ | H or Cl | CF₃ | Cl or H |
| 37 | CF₃ | No₂ | H | H | H | Cl |
| 38 | CF₃ | Br | H | NO₂ | H | H |
| 39 | CF₃ | NO₂ | H | Br | H | H |
| 40 | CF₃ | Cl | H | CF₃ | H | Cl |
| 41 | CF₃ | NO₂ | H | Cl | H | NO₂ |
| 42 | CF₃ | NO₂ | H | Br | H | NO₂ |
| 43 | CF₃ | Cl | H | Cl | H | NO₂ |
| 44 | CF₃ | Cl | H | Br | H | NO₂ |
| 45 | CF₃ | H | Cl | NO₂ | H | NO₂ |
| 46 | CF₃ | NO₂ | Cl | CF₃ | H | NO₂ |
| 47 | CF₃ | Cl | H | NO₂ | Cl | Br |
| 48 | CF₃ | CN | H | NO₂ | H | H |
| 49 | CF₃ | H | CF₃ | NO₂ | H | H |
| 50 | CF₃ | H | Cl | Cl | H | Cl |
| 51 | CF₃ | NO₂ | H | Cl | H | Br |
| 52 | CF₃ | H | Cl | Cl | H | H |

The diphenylamine derivatives according to the invention may be prepared by a variety of processes. Thus a compound of formula:

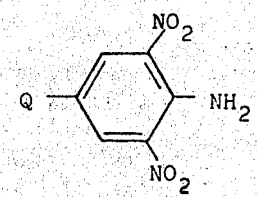

may be treated with a compound of formula:

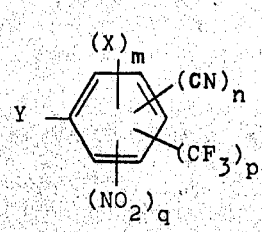

wherein Y represents a halogen atom, and Q, X, $m$, $n$, $p$ and $q$ are as defined hereinabove, to obtain the diphenylamine derivatives. Alternatively, the diphenylamine derivatives may be prepared by treating a compound of formula:

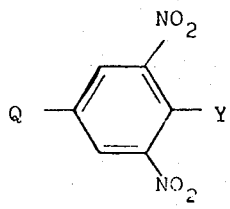

with a compound of formula:

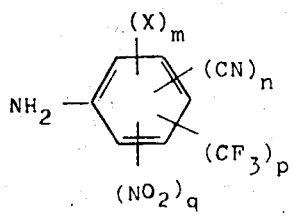

wherein Q, X, Y, $m$, $n$, $p$ and $q$ are as defined hereinabove. These processes may in some cases be carried out by heating the reactants together in the absence of a diluent, and/or a base, but preferably a solvent, or diluent is present. Suitable solvents include, for example, non-hydroxylic materials such as dimethylformamide, dimethylsulphoxide, sulpholane, acetonitrile, and tetrahydrofuran. Of these dimethylformamide is particularly preferred. Hydroxylated solvents, for example methanol and ethanol, may be used in certain circumstances when the presence of the hydroxyl group does not interfere with the progress of the reaction. Suitable bases include sodium hydride (although not when a hydroxylated solvent or diluent is used), alkali metal carbonates, such as potassium carbonate, and alkali metal hydroxides such as potassium hydroxide. The temperature at which the reaction may be carried out will depend upon the choice of reactants, solvent or diluent and base. When dimethylformamide and sodium hydride are used the reaction generally takes place in the range $-10°C$ to $+30°C$, but higher temperatures up to $100°C$ may be employed when other bases are used.

The process generally consists of dissolving or suspending the reactant bearing the amino group in a solvent or diluent in the presence of the base, allowing the base to react with the reactant by the removal of a proton from the amino group, and thereafter adding the second reactant. After allowing a period of time for the reaction to occur the product may be isolated by dilution with a diluent in which the product is insoluble, usually water, which causes the product to precipitate out. The product may then be separated by filtration and recrystallised from a suitable recrystallising solvent or mixture of solvents to yield the product in a substantially pure state.

Other methods of preparation may also be used. Certain of the compounds which bear halogen substituents may be obtained by halogenation of diphenylamine derivatives already bearing the other substituents. Also those bearing nitro substituents may be obtained by the careful nitration of the appropriate diphenylamine derivatives without nitrosubstituents. Again extra halo and/or nitro substituents may be introduced into compounds already bearing such substituents.

These nitration and halogenation processes may be carried out manner well known in the art for the nitration and halogenation of benzenoid aromatic substances.

These nitration and/or halogenation steps may be carried out on compounds which are already within the scope of the invention, or on diphenylamine derivatives outside the scope of which the following examples are thought to be previously unknown:
4,4'-bistrifluoromethyl-2,6-dinitrodiphenylamine (m.p. 174°–176°C),
4'-trifluoromethyl-2,4,6-trinitrodiphenylamine (m.p. 170°–171°C),
4-cyano-4'-trifluoromethyl-2,6-dinitrodiphenylamine (m.p. 216°–219°C),
4'-cyano-4-trifluoromethyl-2,6-dinitrodiphenylamine (m.p. 148°–150°C),
4-trifluoromethyl-2,4',6-trinitrodiphenylamine (m.p. 181°–182°C),
4-trifluoromethyl-2,2',6-trinitrodiphenylamine (m.p. 167°–168°C), and
4'-chloro-4-trifluoromethyl-2,6-dinitrodiphenylamine (m.p. 99°–100°C).

All the intermediate diphenylamines may be made by a process similar to that outlined above for the compounds according to the invention.

The invention also includes pesticidal compositions comprising a diphenylamine derivative of the invention and also comprising a diluent or carrier.

The compositions may be in the form of dusting powders wherein the active ingredient is mixed with a solid diluent or carrier, for example, kaolin, bentonite, kieselguhr, or talc, or they may be in the form of granules, wherein the active ingredient is absorbed on a porous granular material, for example pumice.

Alternatively, the compositions may be in the form of liquid preparations to be used as dips, or sprays, which are generally aqueous dispersions or emulsions of the active ingredient in the presence of one or more known wetting agents, dispersing agents or emulsifying agents. These compositions are prepared by dissolving the active ingredient in a suitable solvent, for example, a ketonic solvent, such as diacetone alcohol, and adding the mixture so obtained to water which may contain one or more known wetting, dispersing or emulsifying agents.

The compositions which are to be used in the form of aqueous dispersions or emulsions are generally supplied in the form of a concentrate containing a high proportion of the active ingredient, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment. The concentrates may contain 10–85% by weight of active ingredient. When diluted to form aqueous preparations, such preparations may contain varying amounts of the active ingredient depending upon the purpose for which they are to be used.

For agricultural or horticultural purposes, the aqueous preparation containing between 0.0001% and 0.1% by weight of the active ingredient may be used.

The compositions of the present invention may, if desired, also comprise in addition to the compound of the invention, at least one other biologically-active ingredient, for example an insecticide or a fungicide.

In use the compositions are applied to the pests, to the locus of the pests, to the habitat of the pests, or to growing plants liable to infestation by the pests, by any of the known means of applying pesticidal compositions for example, by dusting or spraying.

The compounds of the invention and compositions comprising it are very toxic to a wide variety of insect and other invertebrate pests, including, for example, the following:

*Tetranychus telarius* (red spider mites)
*Aphis fabae* (aphids)
*Megoura viceae* (aphids)
*Aedes aegypti* (mosquitos)
*Dysdercus fasciatus* (capsids)
*Musca domestica* (houseflies)
*Blatella germanica* (cockroaches)
*Pieris brassicae* (white butterfly, larvae)
*Plutella maculipennis* (diamond back moth, larvae)
*Phaedon cochleariae* (mustard beetle)
*Calandra granaria* (grain beetle)
*Tribolium confusum* (flour beetle)
*Agriolimax reticulatus* (slugs)

The compounds and compositions of the invention are also useful in the control of fungal pests of plants, including the following:

*Puccinia recondita* (rust of wheat)
*Phytophthora infestans* (blight of tomatoes)
*Plasmopara viticola* (powdery mildew of vines)
*Uncinula necator* (downy mildew of vines)
*Piricularia oryzae* (blast of rice)
*Podosphaera leucotricha* (powdery mildew of apples)

Certain of the compounds of the invention may also be useful in combating virus diseases of plants, The invention is illustrated but not limited by the following examples.

EXAMPLE 1

This example illustrates the preparation of 2,6-dichloro-4'-trifluoromethyl-2',4',6'-trinitrodiphenylamine, (compound No. 1, Table 1).

A solution of 2,6-dichloro-4-nitroaniline (3.75 g) in dry dimethylformamide (30 ml) was added dropwise to a stirred suspension of sodium hydride (0.865g) in dry dimethylformamide (20 ml) at 0°C under a nitrogen atmosphere. The mixture was allowed to warm to the ambient temperature (ca 24°C) for one hour when the addition had been completed, after which it was re-cooled to 10°C. A solution of 4-chloro-3,5-dinitrobenzotrifluoride (4.87 g) in dry dimethylformamide (30 ml) was then added dropwise whilst the temperature of the mixture was maintained at 10°C by external cooling. When this addition had been completed, the mixture was allowed to warm to the ambient temperature and stirred for 48 hours, after which it was poured into an ice/salt/water mixture which was acidified with dilute hydrochloric acid to pH 3. The yellow solid precipitate was collected by filtration, dried in air and recrystallised from a dichloromethane/petroleum ether (boiling range 40°–60°C) mixture to yield 2,6-dichloro-4'-trifluoromethyl-2',4',6'-trinitrodiphenylamine, having a melting point of 139°–141°C.

$C_{13}H_5Cl_2F_3N_4O_6$ requires: C, 35.4; H, 1.13; N, 12.7%. Found: C, 35.46; H, 1.15; ; N, 12.73%.

EXAMPLE 2

This example illustrates the preparation of 4'-cyano-3,5-dichloro-2',4',6'-trinitrodiphenylamine.

2.6-dichloro-4-nitroaniline (3.75 g) was dissolved in dry dimethylformamide (30 ml) and added dropwise to a stirred suspension of sodium hydride (0.86 g) in dry dimethylformamide (30 ml) under a nitrogen atmosphere, whilst maintaining the mixture temperature in the range 0° to 5°C. When the addition was complete, the mixture was allowed to warm to the ambient temperature (ca 22°C) for 30 minutes, after which it was cooled to 10°C and a solution of 4-chloro-3,5-dinitrobenzonitrile (4.1 g) in dry dimethylformamide (30 ml) added dropwise. After completing the addition the mixture was kept at the ambient temperature for 48 hours, and then poured into a mixture of ice, salt and water (total volume 800 ml) and acidified with dilute hydrochloric acid. The resulting precipitate was collected by filtration and recrystallised from a mixture of dichloromethane and petroleum ether (boiling range 40° – 60°C) to yield 4'-cyano-3,5-dichloro-2',4',6'-trinitrodiphenylamine, having a melting point of 240.1° to 241.9°C.

EXAMPLE 3

This example illustrates the preparation of 2,4,6-trichloro-4'-trifluoromethyl-2',6'-dinitrodiphenylamine, (compound No. 5, Table 1).

2,4,6-Trichloroaniline (3.93 g) was dissolved in dry dimethylformamide (30 ml) and added dropwise to a stirred suspension of sodium hydride (0.86 g) in dry dimethylformamide (30 ml) under a nitrogen atmosphere, whilst maintaining the mixture temperature in the range 0° to 5°C. When the addition was complete the mixture was allowed to warm to the ambient temperature (ca 22°C) for 30 minutes. after which it was cooled to 10°C and a solution of 4-chloro-3,5-dinitrobenzotrifluoride (5.41 g) in dry dimethyl-formamide (30 ml) added dropwise. After completing the addition the mixture was kept at the ambient temperature for 48 hours, and then poured into a mixture of ice, salt and water (total volume 800 ml) and acidified with dilute hydrochloric acid. The resulting precipitate was collected by filtration and recrystallised from a mixture of dichloromethane and petroleum ether (boiling range 40° – 60°C) to yield 2,4,6-trichloro-4'-trifluoromethyl-2',6'-dinitrodiphenylamine, having a melting point of 142.8°C to 144.2°C.

EXAMPLE 4

This example illustrates the preparation of 2',4-bis(-trifluoromethyl)-2,4',6'-trinitrodiphenylamine, (compound No. 4, Table 1).

2-Trifluoromethyl-4-nitroaniline (4.12 g) was dissolved in dry dimethylformamide (30 ml) and added dropwise to a stirred suspension of sodium hydride (0.86 g) in dry dimethylformamide (30 ml) under a nitrogen atmosphere, whilst maintaining the mixture temperature in the range of 0° t 5°C. When the addition was complete the mixture was allowed to warm to the ambient temperature (ca 22°C) for 30 minutes, after which it was cooled to 10°C and a solution 4-chloro-3,5-dinitrobenzotrichloride (5.41 g) in dry dimethylformamide (30 ml) added dropwise. After completing the addition the mixture was kept at the ambient temperature for 48 hours, and then poured into a mixture of ice, salt and water (total volume 800 ml) and acidified with dilute hydrochloric acid. The resulting precipitate was collected by filtration and recrystallised from a mixture of dichloromethane and petroleum ether (boiling range 40° – 60°C) to yield 2',4-bis(trifluoromethyl)-2,4'-6-trinitrodiphenylamine, having a melting point of 124.6° to 125.0°C.

EXAMPLE 5

This example illustrates the preparation of 3,5-bis(trifluoromethyl)-2'4',6'-trinitrodiphenylamine To a solution of 3,5-bis(trifluoromethyl) aniline (5.7g) and picryl chloride (7.7g, 80% pure) in dry dimethylformamide (20 ml) was added anhydrous potassium carbonate (2.0g) and the mixture was stirred at 50° – 60°C for 2 hours, after which it was allowed to cool to the ambient temperature and left without stirring for 16 hours. The mixture was then poured into water (200 ml) and the whole acidified with concentrated hydrochloric acid to about pH 1. The precipitated solid was separated by decantation, and washed with water, after which it was collected by filtration and recrystallised from ethanol to give 3,5-bis(trifluoromethyl)-2',4',6'-trinitrodiphenylamine, as yellow crystals having a melting point of 175°–176°C.

EXAMPLE 6

This example illustrates the preparation of 6'-chloro-4-trifluoromethyl-2,2',4',6-tetranitrodiphenylamine, (compound No. 11, Table 1)

2-Chloro-4,6-dinitroaniline (4.35 g) was dissolved in dry dimethylformamide (30 ml) and added dropwise to a stirred suspension of sodium hydride (0.86 g) in dry dimethylformamide (30 ml) under a nitrogen atmosphere, whilst maintaining the mixture temperature in the range 0° to 5°C. When the addition was complete the mixture was allowed to warm to the ambient temperature (ca 22°C) for 30 minutes, after which it was cooled to 10°C and a solution of 4-chloro-3,5-dinitrobenzotrifluoride (5.41 g) in dry dimethylformamide (30 ml) added dropwise. After completing the addition, the mixture was kept at the ambient temperature for 48 hours and then poured into a mixture of ice, salt and water (total volume 800 ml) and acidified with dilute hydrochloric acid. The resulting precipitate was collected by filtration and recrystallised from a mixture of dichloromethane and petroleum ether (boiling range 40° – 60°C) to yield 6'-chloro-4-trifluoromethyl-2,2',-4',6-tetranitrodiphenylamine, having a melting point of 136° to 138°C.

EXAMPLE 7

This example illustrates the preparation of 4,4'-bistrifluoromethyl-2,6-dinitrodiphenylamine, useful as an intermediate in the preparation of diphenylamine derivatives according to the invention.

A mixture of 4-chloro-3,5-dinitrobenzotrifluoride (3.0 g), 4-aminobenzotrifluoride (1.8 g), anhydrous potassium carbonate (1.53 g) and ethanol (35 ml) was refluxed for two hours, and then stirred at the ambient temperature for 16 hours. The mixture was then poured into iced water (500 ml), and the solid precipitate which formed was collected by filtration, dried and recrystallised from a mixture of methylene dichloride, and n-hexane to yield 4,4'-bistrifluoromethyl-2,6-dinitrodiphenylamine, as yellow crystals, melting point 174°–176°C.

EXAMPLE 8

This example illustrates the preparation of 4'-trifluoromethyl-2,4,6-trinitrodiphenylamine useful as an intermediate in the preparation of invention compounds.

A mixture of 4-aminobenzotrifluoride (2.16 g), picryl chloride (3.3 g), anhydrous potassium carbonate (1.8 ), and ethanol (50 ml) was refluxed for 7 hours and then poured into iced water. The precipitated solid was collected by filtration and recrystallised from a mixture of methylene dichloride and petroleum ether (boiling range 40°–60°C) to yield 4'-trifluoromethyl-2,4,6-trinitrodiphenylamine, yellow crystals, melting point 170°–171°C.

EXAMPLE 9

This example illustrated the preparation of 4,4'-bistrifluoromethyl-2,2',6,6'-tetranitrodiphenylamine (compound No. 13, Table 1).

4,4'-Bistrifluoromethyl-2,6-dinitrodiphenylamine (1.5 g) was dissolved in concentrated sulphuris acid (98% w/v, 15 ml) and the solution cooled to 0°C. A mixture of fuming nitric acid (4.0 ml) and concentrated sulphuric acid (8.0 ml) cooled to 0°C was added dropwise with stirring to the amine solution, after which the temperature of the mixture was maintained in the range 0°–5°C for two hours and then at the ambient temperature for one hour. The mixture was then carefully poured into iced water and the resultant precipitate collected by filtration, washed with water and dried to yield 4,4'-bistrifluoromethyl-2,2',6,6'-tetranitrodiphenylamine, yellow crystals, melting in the range 175°–180°C.

EXAMPLE 10

This example illustrated the preparation of 4-cyano-2,6-dinitro-4'-trifluoromethyldiphenylamine, useful as an intermediate in the preparation of the invention compounds.

A mixture of 4-aminobenzotrifluoride (4.0g), 4-chloro-3,5-dinitrobenzonitrile (5.8 g), anhydrous potassium carbonate (3.45 g) and ethanol (50 ml) was refluxed for 6 hours, and then poured into iced water. The precipitate which formed was collected by filtration and recrystallised from ethanol to yield 4-cyano-2,6-dinitro-4'-trifluoromethyldiphenylamine as yellow crystals, melting point 216°–219°C.

EXAMPLE 11

This example illustrates the preparation of 2'-chloro-4'-trifluoromethyl-2,4,6-trinitrodiphenylamine (compound No. 14, Table 1).

A mixture of 4'-trifluoromethyl-2,4,6-trinitrodiphenylamine (1.5 g) and sulphuryl chloride (10.0 ml) was refluxed for 17 hours and then stirred for 80 hours at the ambient temperature, after which the mixture was poured into iced water. The precipitated solid was collected by filtration and recrystallised from a mixture of methylene dichloride and petroleum ether (boiling range 40°–60°C) to yield 2'-chloro-4'-trifluoromethyl-2,4,6-trinitrodiphenylamine, melting point 139.5°–142°C.

EXAMPLE 12

This example illustrates the preparation of 2',5'-dichloro-4-trifluoromethyl-2,4',6-trinitrodiphenylamine (compound No. 16 of Table 1).

Powdered potassium hydroxide (0.5 g) was added to a stirred mixture of 2,5-dichloro-4-nitroaniline (1.0 g) and dry dimethylformamide (3.0 ml) at the ambient temperature. The stirring was continued for 30 minutes, after which 4-chloro-3,5-dinitrobenzotrifluoride (1.5 g) was added in small portions whilst stirring was continued for a further 30 minutes. Concentrated hydrochloric acid (0.5 ml) was then added to the mixture, followed by ethanol (10.0 ml). The precipitated solid was collected by filtration and recrystallised from a mixture of ethanol and ethyl acetate to yield 2′,5′-dichloro-4-trifluoromethyl-2,4′,6-trinitrodiphenylamine, melting point 185°C.

EXAMPLE 13

This example illustrates the preparation of 4-cyano-2′,6′-dibromo-2,6-dinitro-4′-trifluoromethyldiphenylamine (compound No. 17 Table 1).

A mixture of 4-cyano-2′,6′-dibromo-2,6-dinitro-4′-trifluoromethyldiphenylamine (0.5 g), sodium acetate (2.0 g) and glacial acetic acid (20 ml) was heated to 90°C, and a solution of bromine (0.5 g) in glacial acetic acid (10 ml) added dropwise to the stirred mixture. When the addition had been completed the mixture was stirred at 70°–80°C for a further 90 minutes and then poured into iced water. The precipitate which formed was collected by filtration and recrystallised from ethanol to yield 4-cyano-2′,6′-dibromo-2,6-dinitro-4′-trifluoromethyldiphenylamine, melting point 231°–233°C.

EXAMPLE 14

This example illustrates the preparation of 2,6-dinitro-3′,4,5′-tristrifluoromethyldiphenylamine (compound No. 22 of Table 1).

A mixture of 4-chloro-3,5-dinitrobenzotrifluoride (5.0 g), 3,5-bistrifluoromethylaniline (5.0 g), anhydrous potassium carbonate (2.5 g) and dimethylformamide (40 ml) was heated to 50°–70°C for 24 hours and then poured into iced water. Collection of the precipitate by filtration and recrystallisation from methanol yielded 2,6-dinitro-3′,4,5′-tristrifluoromethyldiphenylamine, melting point 147°–148°C.

EXAMPLE 15

This example illustrates the preparation of 2,3,6-trichloro-2′,4,6′-trinitro-4′-trifluoromethyldiphenylamine (compound No. 29 Table 1).

Chlorine gas was passed into a mixture of 2′,5′-dichloro-4-trifluoromethyl-2,4′,6-trinitrodiphenylamine (2.0g), glacial acetic acid (20 ml) and ferric chloride (20 mg) for 12 hours at 30°C., and thereafter for 8 hours at 60°C. The mixture was then poured into iced water, and the precipitate which formed collected by filtration and recrystallised from a mixture of methylene dichloride and petroleum ether (boiling range 40°–60°C) to yield 2,3,6-trichloro-2′,4,6′-trinitro-4′-trifluoromethyldiphenylamine, melting at 141°–143.5°C.

EXAMPLE 16

This example illustrates the preparation of a compound believed to be either 2,2′,4′,6-tetranitro-3′,4,5′-tristrifluoromethyldiphenylamine or 2,2′,6,6′-tetranitro-3′,4,5′-tristrifluoromethyldiphenylamine (compound No. 27 Table 1).

To a stirred solution of 2,6-dinitro-3′,4,5′-tristrifluoromethyldiphenylamine (0.6 g) in concentrated sulphuric acid (98% w/v, 20 ml) maintained at 0°C, was carefully added fuming nitric acid (2.0 ml) over a period of 10 minutes. After the addition was complete, stirring was continued for a further 30 minutes, and the mixture was then poured carefully into iced water. The precipitate which formed was collected by filtration, washed with water and recrystallised from industrial methylated spirit to yield a compound of melting point 197°–198°C, believed to be either 2,2′,4′,6 or 2,2′,6,6′-tetranitro-3′,4,5′-tristrifluoromethyldiphenylamine.

EXAMPLE 17

The procedure illustrated in Example 12 was used to prepare the following compounds from the appropriate intermediates:

| Compound No. (Table 1) | Melting Point °C |
|---|---|
| 1 | 139–141 |
| 31 | 197–199 |
| 45 | 176–177 |
| 46 | 158–159 |
| 51 | 174–176 |
| 52 | 138–139 |

EXAMPLE 18

The procedure illustrated in Example 1 was used to prepare the following compounds from the appropriate intermediates:

| Compound No. (Table 1) | Melting point °C | Compound No. (Table 1) | Melting point °C |
|---|---|---|---|
| 3 | 201–201.5 | 16 | 183–185 |
| 6 | 194–195 | 33 | 147–150 |
| 7 | 144–146 | 38 | 177–178 |
| 8 | 146–148 | 39 | 136–138 |
| 9 | 148–148.5 | 48 | 154–155 |
| 10 | 152–153 | 49 | 183 |
| 12 | 165–166 | 50 | 164 |

EXAMPLE 19

4-trifluoromethyl-2,2′,6-trinitrodiphenylamine, useful as an intermediate in the preparation of compounds according to the invention was prepared by a procedure similar to that illustrated in Example 12 from 2-nitroaniline and 4-chloro-3,5-dinitrobenzotrifluoride. The product had a melting point of 167°–168°C.

EXAMPLE 20

The procedure illustrated in Example 13 was used to prepare the following compounds from the appropriate non-brominated intermediates:

| Compound No. (Table 1) | Melting Point °C |
|---|---|
| 18 | 163–164 |
| 19 | 201 |
| 22 | 197–198 |
| 25 | 191–192 |
| 26 | 143–144 |
| 28 | 164–165 |
| 47 | 149–150 |

EXAMPLE 21

The procedure illustrated in Example 14 was used to prepare the following compounds from the appropriate intermediates:

3,5-bistrifluoromethyl-2',4',6'-trinitrodiphenylamine (compoud No. 32, Table 1), melting point 175°–176°C; and 4-trifluoromethyl-2,4',6-trinitrodiphenylamine (melting point 181°–182°C), 4-trifluoromethyl-2,2',6-trinitrodiphenylamine (melting point 170°–171°C) and 4'-chloro-2,6-dinitro-4-trifluoromethyldiphenylamine (melting point 99°–100°C), the latter three compounds being useful as intermediates in the preparation of diphenylamine derivatives according to the invention.

EXAMPLE 22

The procedure of Example 15 was also used to prepare Compound No. 37 of Table 1 from 4-trifluoromethyl-2,2',6-trinitrodiphenylamine. The product had a melting point of 100°–110°C.

EXAMPLE 23

The procedure of Example 16 was used to prepare Compound No. 15 of Table 1 from 4-cyano-2,6-dinitro-4'-trifluoromethyldiphenylamine. The product had a melting point of 169°–171°C.

EXAMPLE 24

This example illustrates the preparation of 2',4-bistrifluoromethyl-6'-chloro-2,4',6-trinitrodiphenylamine (compound No. 35 of Table 1).

Chlorine gas was passed for 4 hours into a solution of 2',4-bistrifluoromethyl-2,4',6-trinitrodiphenylamine (40.0 g) in concentrated sulphuric acid (98% w/v, 400 ml) whilst the temperature was maintained at 50°C, after which the mixture was stirred at the ambient temperature for 18 hours. The mixture was then carefully poured into iced water, and the precipitated solid collected by filtration and recrystallised from a mixture of ethanol and acetone to yield 2',4-bistrifluoromethyl-6-chloro-2,4',6-trinitrodiphenylamine, melting point 117°–119°C.

EXAMPLE 25

The procedure of Example 24 was used to prepare the following compounds from the appropriate non-chlorinated intermediates:

| Compound No. (Table 1) | Melting point °C |
| --- | --- |
| 36 | 150–152 |
| 40 | 114–115 |
| 43 | 155–157 |
| 44 | 178–179 |

EXAMPLE 26

The procedure of Example 9 was used to prepare the following compounds from the appropriate intermediates as follows:

Compound No. 20 (Table 1), melting point 181°–182°C, from 2,2',4',6-tetranitro-4-trifluoromethyldiphenylamine;

Compound No. 21 (Table 1), melting point 98°–99°C, from 4-cyano-2'-trifluoromethyl-2,4',6-trinitrodiphenylamine;

Compound No. 24 (Table 1), melting point 161°–162°C, from 2',4-bistrifluoromethyl-2,4',6-trinitrodiphenylamine;

Compound No. 34 (Table 1), melting point 206°–208°C, from 2',4',dichloro-2,6-dinitro-4-trifluoromethyldiphenylamine;

Compound No. 41, (Table 1), melting point 168°–170°C, from 4'-chloro-2,6-dinitro-4-trifluoromethyldiphenylamine; and compound No. 42 (Table 1), melting point 202°–203°C, from 4'-bromo-2,2',6-trinitro-4-trifluoromethyldiphenylamine.

EXAMPLE 27

5 parts by weight of Compound No. 1 of Table 1 were thoroughly mixed in a suitable mixer with 95 parts by weight of talc. There was thus obtained a dusting powder.

EXAMPLE 28

10 parts by weight of Compound No. 2 of Table 1, 10 parts of an ethylene oxide-octyl-phenol condensate ("Lissapol" NX: "Lissapol" is a Trade Mark) and 80 parts by weight of diacetone alcohol were thoroughly mixed. There was thus obtained a concentrate which, on mixing with water, gave an aqueous dispersion suitable for application as a spray in the control of insect pests.

EXAMPLE 29

A granular composition was prepared by dissolving the active ingredient in a solvent, spraying the solution obtained on to the granules of pumice and allowing the solvent to evaporate.

|  | %wt |
| --- | --- |
| Compound No. 3 of Table 1 | 5 |
| Pumice Granules | 95 |
|  | 100 % |

EXAMPLE 30

An aqueous dispersion formulation was prepared by mixing and grinding the ingredients recited below in the proportions stated.

|  | %wt |
| --- | --- |
| Compound No. 4 of Table 1 | 40 |
| Calcium lignosulphonate | 10 |
| Water | 50 |
|  | 100 % |

EXAMPLE 31

By procedures similar to those illustrated in Examples 27 to 30 pesticidal compositions incorporating as active ingredients any one of the diphenylamine derivatives set out in Table 1 above may be obtained.

EXAMPLE 32

The activity of the diphenylamine derivatives of the present invention was shown in tests against a variety of insect and other invertebrate pests. The compound was used in the form of a liquid preparation containing 0.1% by weight of the compound except in the tests with Aedes aegypti where the preparations contained 0.01% by weight of the compound. The preparations were made by dissolving the compounds in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "Lissapol" is a Trade Mark.

The test procedure adopted with regard to each pest was basically the same and comprised supporting a number of pests on a medium which was usually a host plant or a foodstuff on which the pests feed, and treating either or both the pests and the medium with the preparations.

The mortality of the pests was then assessed at periods usually varying from one to three days after the treatment.

The results of the tests are given below in Table 2. In this table the first column indicates the name of the pest species.

Each of the subsequent columns indicates the host plant or medium on which it was supported, the number of days which were allowed to elapse after the treatment before assessing the mortality of the pests, and the results obtained for each compound. The assessment is expressed in integers which range from 0 – 3.

0 represents less than 30% kill
1 represents 30–49% kill
2 represents 50–90% kill
3 represents over 90% kill In the Table "contact test" indicates that both the pests and the medium were treated, "residual test" indicates that the medium was treated before infestation with the pests.

TABLE 2

| Pest Species | Support medium | No. of days | 1 | 2 | 3 | 4 | 5 | 6 | 7 | 8 | 11 | 12 | 13 | 14 | 15 | 16 | 17 | 18 |
|---|---|---|---|---|---|---|---|---|---|---|---|---|---|---|---|---|---|---|
| *Tetranychus telarius* (red spider mites, adults) | French Bean | 3 | 3 | 3 | 3 | 3 | 2 | 0 | 0 | 0 | 3 | 0 | 2 | 0 | 0 | 0 | 0 | 3 |
| *Tetranychus telarius* (red spider mites, eggs) | French Bean | 3 | 3 | 3 | 3 | 0 | 3 | 0 | 0 | 0 | 0 | 0 | 3 | 0 | 0 | 0 | 0 | 2 |
| *Aphis fabae* (green aphids) | Broad Bean | 2 | 3 | 0 | 1 | 3 | 3 | 2 | 0 | 0 | 0 | 0 | 3 | 0 | 0 | 0 | 0 | 3 |
| *Megoura viceae* (black aphids) | Broad Bean | 2 | 3 | — | 0 | 3 | 3 | 0 | 0 | 0 | 0 | 0 | 3 | 0 | 0 | 0 | 0 | 3 |
| *Aedes aegypti* (mosquito adults) | Plywood | 1 | 2 | 0 | 0 | 0 | 0 | 0 | 0 | 0 | 0 | 0 | 0 | 0 | 0 | 0 | 0 | 2 |
| *Musca domestica* (houseflies - contact test*) | Milk/sugar | 2 | 3 | 1 | 3 | 3 | 3 | 0 | 3 | 3 | 3 | 3 | 0 | 3 | 0 | 3 | 3 | 3 |
| *Musca domestica* (houseflies - residual test*) | Plywood | 2 | 3 | 0 | 0 | 2 | 0 | 0 | 0 | 0 | 0 | 0 | 0 | 0 | 0 | 1 | 0 | 1 |
| *Pieris brassicae* (cabbage white caterpillars) contact test | Cabbage | 2 | 3 | 3 | 0 | 3 | 3 | 0 | 0 | 0 | 3 | 2 | 2 | 0 | 0 | 2 | 0 | 3 |
| *Plutella maculipennis* (diamond back moth, larvae) contact test | Mustard | 2 | 3 | 0 | 2 | 2 | 0 | 0 | 1 | 1 | 1 | 1 | 0 | 0 | 0 | 0 | 0 | 0 |
| *Phaedon cochleariae* (mustard beetles)- residual test | Mustard | 2 | 3 | 0 | 0 | 0 | 1 | 0 | 0 | 0 | 3 | 2 | 2 | 0 | 0 | 0 | 3 | 3 |
| *Calandra granaria* (grain beetles) | Grain | 2 | 2 | 0 | 0 | 0 | 0 | 0 | 0 | 0 | 0 | 0 | 0 | 0 | 0 | 0 | 0 | 0 |
| *Tribolium confusum* (flour beetles) | Grain | 2 | 2 | 0 | 0 | 0 | 0 | 0 | 0 | 0 | 2 | 1 | 0 | 2 | 0 | 2 | 1 | 3 |
| *Blattella germanica* (cockroaches) | — | 1 | 3 | 0 | 0 | 2 | 0 | 0 | 0 | 0 | 3 | 0 | 0 | 0 | 3 | 0 | 0 | 3 |
| *Meloidogyne incognita* (nematodes) | Water | 1 | — | — | — | — | — | — | 0 | — | — | 3 | — | 3 | 3 | 3 | — | — |
| *Aedes aegypti* (mosquito larvae) | Water | 1 | 3 | 3 | 0 | 3 | 1 | 3 | 0 | 0 | 3 | 3 | 0 | 3 | 0 | 3 | 3 | 3 |
| *Dysdescus fasciatus* (capsid) | Grain | 2 | 3 | 0 | 0 | 2 | 0 | 0 | 0 | 0 | 3 | 0 | 0 | 0 | 3 | 0 | 0 | 3 |

| Pest Species | Support medium | No. of days | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|---|
| *Tetranychus telarius* (red spider mites, adults) | French Bean | 3 | 0 | 0 | 0 | 3 | 3 | 0 | 3 | 3 | 0 | 3 | 3 | 3 | 3 | 3 | 0 | 0 | 3 | 3 |
| *Tetranychus telarius* (red spider mites, eggs) | French Bean | 3 | 0 | 0 | 0 | 3 | 3 | 0 | 3 | 3 | 0 | 3 | 3 | 3 | 3 | 3 | 0 | 1 | 3 | 3 |
| *Aphis fabae* (green aphids) | Broad Bean | 2 | 0 | 0 | 0 | 0 | 0 | 0 | 0 | 3 | 0 | 0 | 3 | 3 | 3 | 2 | 0 | 0 | 3 | 3 |
| *Megoura viceae* | Broad | | | | | | | | | | | | | | | | | | | |

TABLE 2-continued

| Pest Species | Support medium | No. of days | 1 | 2 | 3 | 4 | 5 | 6 | 7 | 8 | 11 | 12 | 13 | 14 | 15 | 16 | 17 | 18 |
|---|---|---|---|---|---|---|---|---|---|---|---|---|---|---|---|---|---|---|
| (black aphids) | Bean | 2 | 0 | 0 | 0 | 0 | 0 | 0 | 0 | 3 | 0 | 0 | 3 | 3 | 3 | 2 | 0 | 0 | 3 | 3 |
| *Aedes aegypti* (mosquito adults) | Plywood | 1 | 0 | 0 | 0 | 0 | 0 | 3 | 3 | 3 | 3 | 3 | 3 | 3 | 0 | 0 | 0 | 3 | 3 | 0 |
| *Musca domestica* (houseflies - contact test) | Milk/sugar | 2 | 0 | 0 | 0 | 2 | 3 | 0 | 3 | 3 | 0 | 3 | 3 | 3 | 3 | 3 | 0 | 0 | 3 | 3 |
| *Musca domestica* (houseflies - residual test) | Plywood | 2 | 0 | 0 | 0 | 0 | 0 | 0 | 0 | 1 | 0 | 3 | 0 | 0 | 3 | 0 | 0 | 0 | 2 | 0 |
| *Pieris brassicae* (cabbage white caterpillars) contact test | Cabbage | 2 | 3 | 0 | 0 | 0 | 3 | 0 | 3 | 3 | 0 | 3 | 2 | 3 | 3 | 2 | 0 | 0 | 3 | 2 |
| *Plutella maculipennis* (diamond back moth, larvae) contact test | Mustard | 2 | 0 | 1 | 0 | 0 | 0 | 1 | 1 | 2 | 0 | 3 | 0 | 0 | 3 | 0 | 0 | 0 | 1 | 0 |
| *Phaedon cochleariae* (mustard beetles) residual test | Mustard | 2 | 0 | 1 | 1 | 0 | 1 | 2 | 1 | 2 | 0 | 2 | 0 | 2 | 3 | 0 | 0 | 0 | 3 | 2 |
| *Calandra granaria* (grain beetles) | Grain | 2 | 0 | 0 | 0 | 0 | 0 | 1 | 0 | 0 | 0 | 0 | 0 | 0 | 0 | 0 | 0 | 0 | 3 | 0 |
| *Tribolium confusum* (flour beetles) | Grain | 2 | 0 | 0 | 0 | 0 | 0 | 0 | 0 | 0 | 0 | 0 | 0 | 0 | 0 | 2 | 0 | 0 | 3 | 0 |
| *Blattella germanica* (cockroaches) | — | 1 | 0 | 3 | 0 | 0 | 0 | 0 | 0 | 0 | 0 | 0 | 0 | 3 | 3 | 3 | 0 | 0 | 0 | 0 |
| *Meloidogyne incognita* (nematodes) | Water | 1 | 3 | 3 | 3 | 0 | 3 | 3 | 3 | 3 | — | — | — | — | — | 0 | 0 | — | — | 3 |
| *Aedes aegypti* (mosquito larvae) | Water | 1 | 0 | 3 | 3 | 0 | 3 | 3 | 3 | 3 | 3 | 3 | 3 | 3 | 3 | 0 | 3 | 3 | 3 | 0 |
| *Dysdercus fasciatus* (capsid) | Grain | 2 | 0 | 3 | 0 | 0 | 0 | 0 | 0 | 0 | 0 | 0 | 0 | 3 | 3 | 0 | 0 | 0 | 3 | 0 |

| Pest Species | Support medium | No. of days | 37 | 38 | 39 | 40 | 41 | 42 | 43 | 44 | 46 | 47 | 48 | 49 | 51 | 52 |
|---|---|---|---|---|---|---|---|---|---|---|---|---|---|---|---|---|
| *Tetranychus telarius* (red spider mite, adult) | French Bean | 3 | 3 | 0 | 0 | 3 | 0 | 0 | 3 | 3 | 0 | 3 | 3 | 0 | — | 0 |
| *Tetranychus telarius* (red spider mite, eggs) | French Bean | 3 | 3 | 0 | 0 | 3 | 3 | 2 | 3 | — | 0 | 3 | 3 | 0 | — | 0 |
| *Aphis fabae* (green aphids) | Broad Bean | 2 | 0 | 0 | 0 | 3 | 3 | 2 | 1 | 1 | 0 | 3 | 0 | 0 | — | 0 |
| *Megoura viceae* (black aphids) | Broad Bean | 2 | 0 | 0 | 0 | 3 | 3 | 2 | 2 | 1 | 0 | 3 | 0 | 0 | — | 0 |
| *Aedes aegypti* (mosquito adults) | Plywood | 1 | 3 | 3 | 0 | 3 | 0 | 0 | 1 | 0 | 0 | 3 | 3 | 0 | — | 0 |
| *Musca domestica* (houseflies - contact test) | Milk/sugar | 2 | 3 | 3 | 3 | 3 | 3 | 3 | 3 | 3 | 0 | 0 | 0 | 3 | 3 | 0 |
| *Musca domestica* (houseflies - residual test) | Plywood | 2 | 0 | 0 | 0 | 3 | 0 | 0 | 0 | 0 | 0 | 0 | 2 | 0 | — | 0 |
| *Pieris brassicae* (cabbage white caterpillars) contact test | Cabbage | 2 | 3 | 0 | 0 | 3 | 0 | 0 | 3 | 3 | 0 | 0 | 2 | 0 | — | 0 |
| *Plutella maculipennis* (diamond back moth, larvae) contact test | Mustard | 2 | 2 | 3 | 0 | 3 | 0 | 0 | 0 | 0 | 0 | 0 | 2 | 3 | 2 | 0 |
| *Phaedon cochleariae* (mustard beetles) residual test | Mustard | 2 | 0 | 0 | 0 | 1 | 0 | 0 | 2 | 1 | 0 | 0 | 1 | 0 | — | 0 |
| *Calandra granaria* (grain beetle) | Grain | 2 | 0 | 0 | 0 | 3 | 0 | 0 | 0 | 0 | 0 | 0 | 0 | 0 | — | 0 |
| *Tribolium confusum* (flour beetles) | Grain | 2 | 0 | 0 | 0 | 3 | 0 | 0 | 0 | 0 | 0 | 0 | 0 | 0 | — | 0 |
| *Plattella germanica* (cockroaches) | — | 1 | 0 | 0 | 0 | 3 | 0 | 0 | 0 | 2 | 0 | 0 | 0 | 0 | — | 0 |
| *Meloidogyne incognita* (nematodes) | Water | 1 | — | — | — | — | 0 | 0 | 0 | 0 | 3 | 3 | 3 | 0 | — | 2 |

TABLE 2-continued

| Pest Species | Support medium | No. of days | Compound No (Table 1) | | | | | | | | | | | | | | |
|---|---|---|---|---|---|---|---|---|---|---|---|---|---|---|---|---|---|
| | | | 1 | 2 | 3 | 4 | 5 | 6 | 7 | 8 | 11 | 12 | 13 | 14 | 15 | 16 | 17 | 18 |
| Aedes aegypti (Mosquito larvae) | Water | 1 | 3 | 3 | 0 | 3 | 3 | 3 | 3 | 3 | 0 | 3 | 3 | 3 | — | 0 | | |
| Dysdercus fasciatus (capsid) | Grain | 2 | 0 | 0 | 0 | 3 | 1 | 0 | 0 | 0 | 0 | 3 | 0 | 0 | — | 0 | | |

EXAMPLE 33

The compounds of this invention were tested against a variety of foliar fungal diseases of plants. The technique employed is to spray the foliage of the undiseased plants with a solution of the test compound and also to drench the soil in which the plants are growing with another solution of the of the same test compound. All solutions for spraying and drenching contained 0.01% of the test compound. The plants were then infected with the disease it was desired to control and after a period of days, depending upon the particular disease, the extent of the disease was visually assessed. The results are given in Table 4 below, wherein the extent of the disease is given in the form of a grading as follows:

| Grading | Percentage amount of disease |
|---|---|
| 0 | 61 to 100 |
| 1 | 26 to 60 |
| 2 | 6 to 25 |
| 3 | 0 to 5 |

In Table 3 the disease is given in the first column, and in the second column is given the time which elapsed between infecting the plants and assessing the amount of disease.

TABLE 3

| Disease and Plant | Time Interval (days) | Disease code letter (Table 4) |
|---|---|---|
| Puccinia recondita (wheat) | 10 | A |
| Phytophthora infestans (tomato) | 3 | B |
| Plasmopara viticola (vine) | 7 | C |
| Uncinula necator (vine) | 10 | D |
| Piricularia oryzae (rice) | 7 | E |
| Podosphaera leucotricha (apple) | 10 | F |

TABLE 4

| Compound No. (Table 1) | Disease Code Letter (Table 3) | | | | | |
|---|---|---|---|---|---|---|
| | A | B | C | D | E | F |
| 1 | — | — | 3 | 3 | 0 | 3 |
| 2 | 3 | 3 | 3 | 0 | 0 | 3 |
| 3 | 3 | 3 | 3 | 0 | 0 | 0 |
| 4 | — | 3 | 3 | 3 | — | 3 |
| 5 | 0 | 0 | 0 | 0 | 3 | 0 |
| 6 | 3 | 3 | 3 | 0 | 0 | 0 |
| 7 | 3 | 3 | 3 | 0 | 0 | 0 |
| 8 | 3 | 1 | 3 | 0 | 0 | 0 |
| 9 | 0 | 0 | 0 | 1 | 2 | 1 |
| 10 | 0 | 0 | 0 | 1 | 3 | 0 |

TABLE 4-continued

| Compound No. (Table 1) | Disease Code Letter (Table 3) | | | | | |
|---|---|---|---|---|---|---|
| | A | B | C | D | E | F |
| 11 | 3 | 3 | 3 | 3 | — | 3 |
| 12 | 3 | 3 | 3 | 0 | 0 | 0 |
| 13 | — | 3 | 3 | 1 | — | 3 |
| 14 | 3 | 3 | 3 | 3 | 0 | 0 |
| 15 | 0 | 3 | 1 | 0 | — | 0 |
| 16 | 3 | 3 | 3 | 3 | — | 0 |
| 17 | 0 | 3 | 1 | 1 | 2 | 0 |
| 18 | 1 | 2 | 3 | 3 | — | 3 |
| 19 | 3 | 3 | 3 | 0 | — | 0 |
| 20 | 1 | 0 | 0 | 0 | — | 0 |
| 21 | 2 | 0 | 1 | 0 | 0 | 0 |
| 22 | 3 | 1 | 0 | 1 | 1 | 0 |
| 23 | — | 3 | 3 | 3 | — | 3 |
| 24 | 2 | 3 | 3 | 3 | — | 0 |
| 25 | 3 | 3 | 3 | 3 | — | 0 |
| 26 | 3 | 3 | 3 | 3 | — | 3 |
| 27 | 3 | 2 | 3 | 0 | 0 | 0 |
| 28 | 0 | 3 | 3 | 1 | — | 0 |
| 29 | 3 | 3 | 3 | 3 | — | 3 |
| 30 | 3 | 3 | 3 | 3 | — | 3 |
| 31 | 3 | 3 | 3 | 3 | — | 3 |
| 32 | 3 | 3 | 3 | 3 | — | 1 |
| 33 | 1 | 2 | 3 | 0 | 0 | 0 |
| 34 | 1 | 3 | 1 | 0 | 0 | 0 |
| 35 | 3 | 3 | 3 | 3 | 0 | 3 |
| 36 | 3 | 3 | 3 | 3 | 0 | 0 |
| 38 | 2 | 3 | 3 | 0 | 0 | 0 |
| 39 | 3 | 3 | 2 | 0 | 0 | 0 |
| 40 | 3 | 3 | 3 | 3 | 0 | 3 |
| 41 | 3 | 3 | 3 | 0 | 0 | 0 |
| 42 | 3 | 3 | 3 | 1 | 0 | 0 |
| 43 | 3 | 3 | 3 | 3 | 0 | 3 |
| 44 | 3 | 3 | 3 | 2 | 0 | 3 |
| 45 | 3 | 3 | 3 | 0 | 0 | — |
| 46 | 0 | 3 | 3 | 1 | 0 | 3 |
| 47 | 0 | 3 | 2 | 3 | 0 | 2 |
| 48 | 0 | 3 | 3 | 2 | 0 | 3 |
| 49 | 1 | 1 | 3 | 0 | 0 | 0 |
| 51 | 3 | 3 | 3 | 3 | 0 | — |

I claim:
1. A diphenylamine derivative of formula:

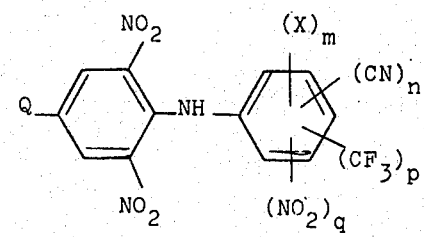

wherein either (a) Q represents a cyano or trifluoromethyl group, and X represents a halogen atom, $m$ is an integer from zero to three, $n$ is zero or one, $p$ is an integer from zero to two, and $q$ is an integer from zero to three, the sum of $m$, $n$, $p$ and $q$ being an integer from two to five; or (b) Q represents a nitro group and X represents a halogen atom, $m$ is an integer from zero to three, $n$ is zero or one, $p$ is an integer from zero to two, and $q$ is an integer from zero to three, the sum of $n$ and $p$ being an integer from one to three, and the sum of $m$, $n$, $p$ and $q$ being an integer from two to five.

2. A diphenylamine derivative according to claim 1 of formula:

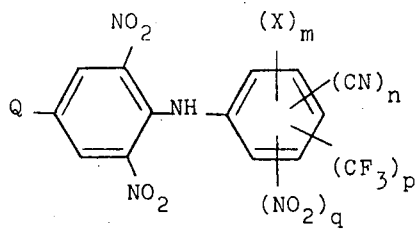

wherein Q represents a cyano or trifluoromethyl group and X represents a halogen atom, $m$ is an integer from zero to three, $n$ is zero or one, $p$ is an integer from zero to two, and $q$ is an integer from zero to three, the sum of $m$, $n$, $p$ and $q$ being an integer from two to five.

3. A diphenylamine derivative according to claim 1 of formula:

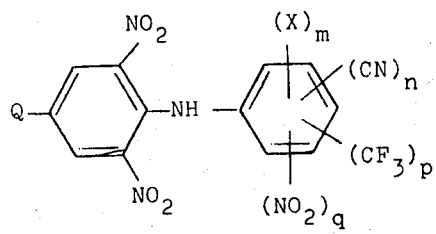

wherein Q represents the trifluoromethyl group and X represents a halogen atom, $m$ is an integer from zero to three, $n$ is zero or one, $p$ is an integer from zero to two, and $q$ is an integer from zero to three, the sum of $m$, $n$, $p$ and $q$ being an integer from two to five.

4. A diphenylamine derivative according to claim 1 of formula:

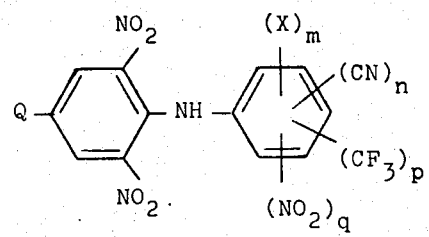

wherein Q represents the nitro group and X represents a halogen atom, $m$ is an integer from zero to three, $n$ is zero or one, $p$ is an integer from zero to two, and $q$ is an integer from zero to three, the sum of $n$ and $p$ being an integer from one to three, and the sum of $m$, $n$, $p$ and $q$ being an integer from two to five.

5. A diphenylamine derivative according to claim 1 and selected from the compound having the formula:

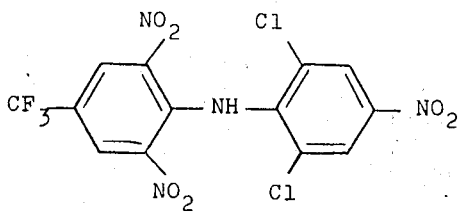

the compound having the formula:

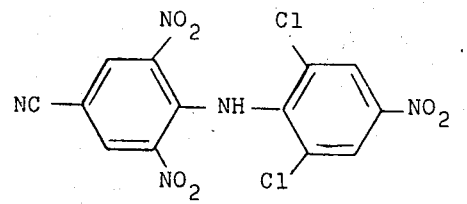

the compound having the formula:

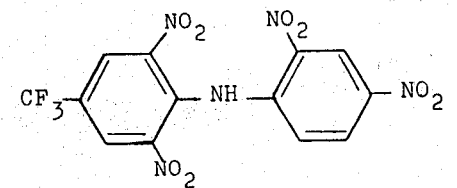

and the compound having the formula:

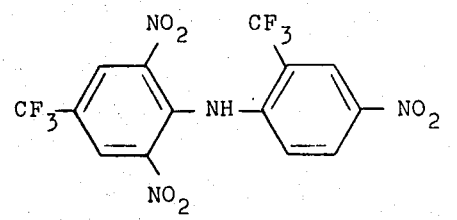

* * * * *